US00PP23478P3

(12) United States Plant Patent
Chimenti

(10) Patent No.: US PP23,478 P3
(45) Date of Patent: Mar. 19, 2013

(54) GRAPE PLANT NAMED 'CHIMENTI GLOBE'

(50) Latin Name: *Vitis vinifera*
Varietal Denomination: Chimenti Globe

(76) Inventor: Alfredo Chimenti, Talagante (CL)

( * ) Notice: Subject to any disclaimer, the term of this patent is extended or adjusted under 35 U.S.C. 154(b) by 0 days.

(21) Appl. No.: 13/199,334

(22) Filed: Aug. 26, 2011

(65) Prior Publication Data

US 2012/0066803 P1 Mar. 15, 2012

(30) Foreign Application Priority Data

Sep. 7, 2010 (CL) ..... 1062

(51) Int. Cl.
*A01H 5/00* (2006.01)

(52) U.S. Cl. ..... Plt./205

(58) Field of Classification Search ..... Plt./205
See application file for complete search history.

*Primary Examiner* — Annette Para

(74) *Attorney, Agent, or Firm* — Morrison & Foerster LLP

(57) ABSTRACT

A new and distinct grape plant variety named 'Chimenti Globe', characterized by the following unique combination of characteristics: a bright light red color that never darkens no matter how advanced its maturity, large seeded berries, sugar level, acidity, and excellent conservation in cold storage.

6 Drawing Sheets

Latin name: Genus and species: *Vitis vinifera.*

Varietal denomination: Variety denomination: 'Chimenti Globe'.

CROSS REFERENCE TO RELATED APPLICATION

The present application claims priority to Chilean Plant Patent Application No. 1062, filed Sep. 7, 2010, which is herein incorporated by reference.

BACKGROUND OF THE INVENTION

The present invention relates to a new and distinct grape plant variety which will hereinafter be denominated as 'Chimenti Globe', and more particularly as a grapevine which produces a large, bright light red color seeded grapes that mature in the southern hemisphere during early March (late summer or early autumn) in the Talagante area of Chile. The new variety resembles 'Red Globe' in almost all features, except for the very distinct characteristic of having a bright light red color of the grapes. This new variety was discovered as a spot mutation in an 18 year old orchard of 'Red Globe' in the area called Talagante, in the Metropolitan Region, in Chile (South America). Upon the 2005 harvest, it was noticed that one branch in a vine had all the clusters with a bright light red color fruit, very appreciated by Asian markets, whereas the rest of the orchard had a strong to deep purplish red color. The vine was marked and the year after, the vine again produced fruit that had a consistently different and attractive bright light red color.

The progeny was first asexually propagated in winter of Year One (July-August) by top grafting two plants of the 27$^{th}$ row of the same orchard with scions. Only plant No. 91 survived, and it became the mother plant of all the rest of the subsequent propagations. During winter of Year Two (July-August), more extensive propagation took place by top working with dormant scions, in the same row a total of 18 additional plants. Further propagation of these plants was made on winter dormant season of Year Three for a total of 166 plants. The location of the original plant and subsequent propagation and trail blocks is: Camino Loreto, Parcelas 8 y 9 Santa Ana, Comuna de Talagante, Santiago, Región Metropolitana, Chile.

The original grape plant and progeny have been observed growing in a cultivated area of Talagante, Comuna de Talagante, Metropolitan Region of Chile.

The first observed fruiting of the propagated plant occurred in season of Year Two to Year Three with mature fruit observed in March of Year Three.

BRIEF SUMMARY OF THE INVENTION

The 'Chimenti Globe' variety is distinguished from 'Red Globe' and other grape plant varieties by the following unique combination of characteristics: a bright light red color that never darkens no matter how advanced its maturity, large seeded berries, sugar level, acidity, and excellent conservation in cold storage.

Asexual reproduction of this new variety by dormant scion top grafting shows that the foregoing and all other characteristics and distinctions come true to form and are established and transmitted through succeeding propagations.

Figure 1:
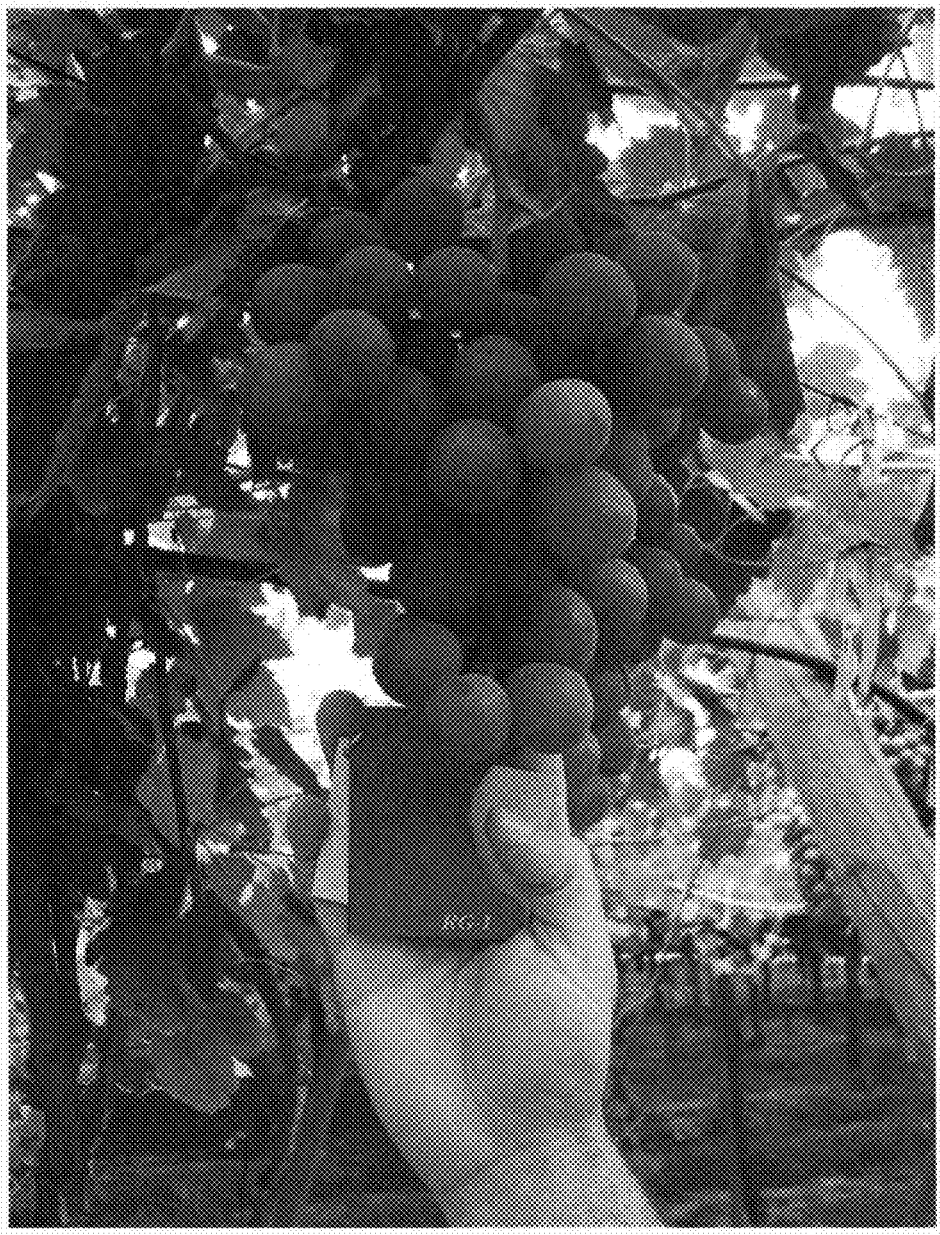
FIG. 1 shows a single 'Chimenti Globe' grape cluster.
Figure 2:
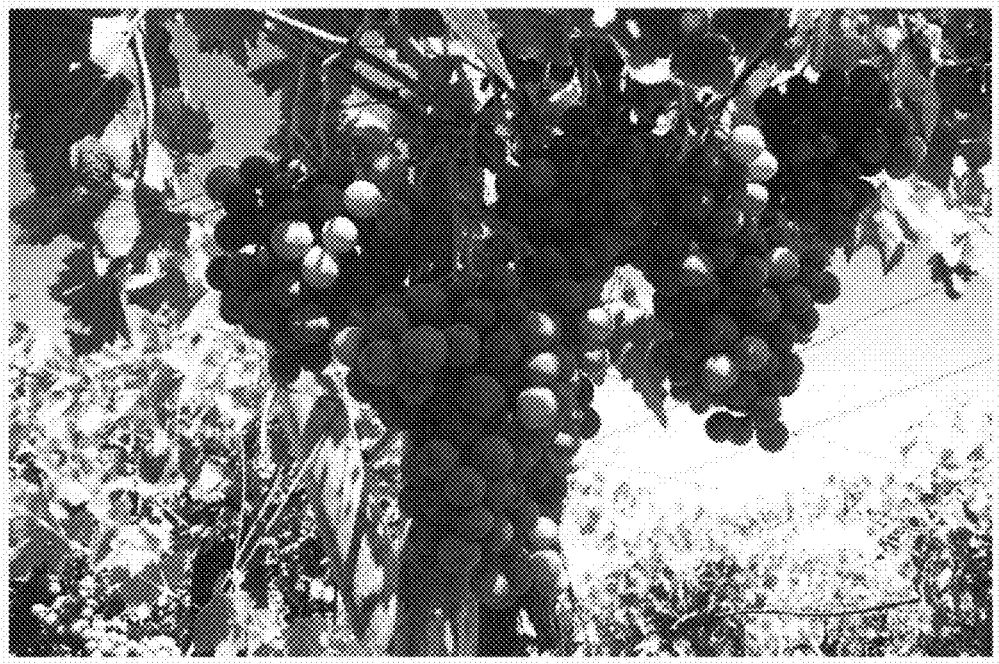
FIG. 2 shows multiple 'Chimenti Globe' grape clusters.
Figure 3:
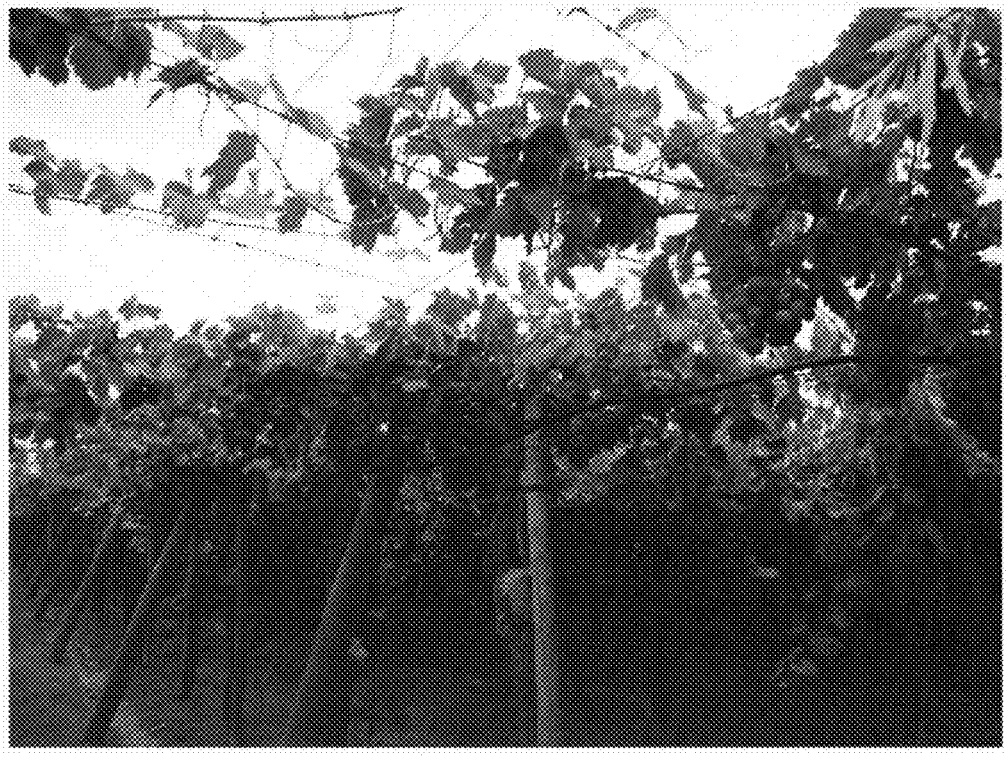
FIG. 3 shows 'Chimenti Globe' plant vine.
Figure 4:
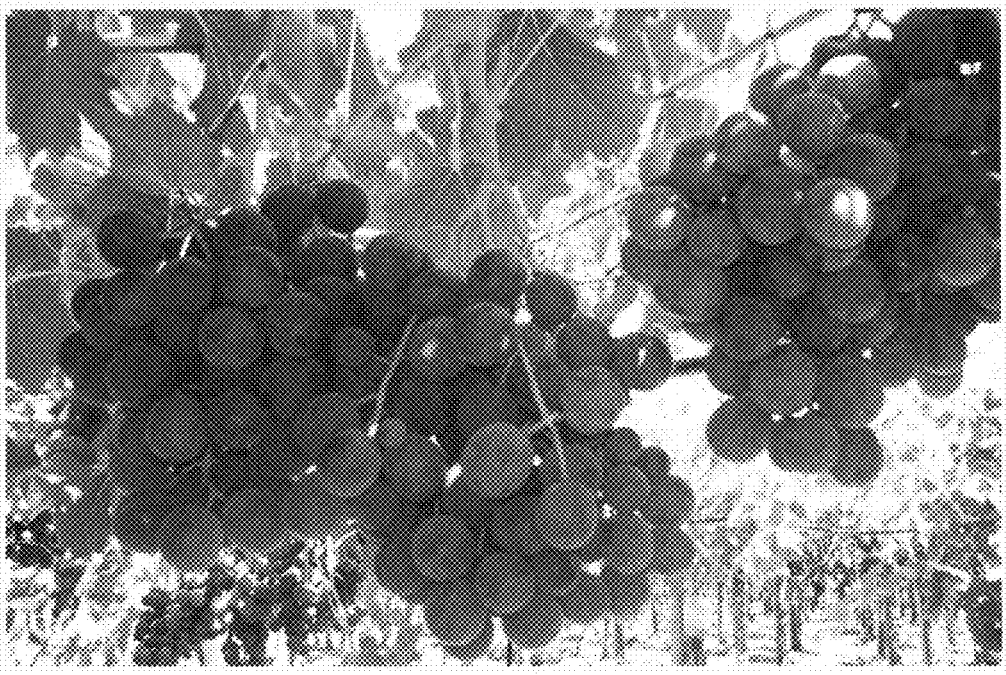
FIG. 4 shows 'Chimenti Globe' plant shoot.
Figure 5:
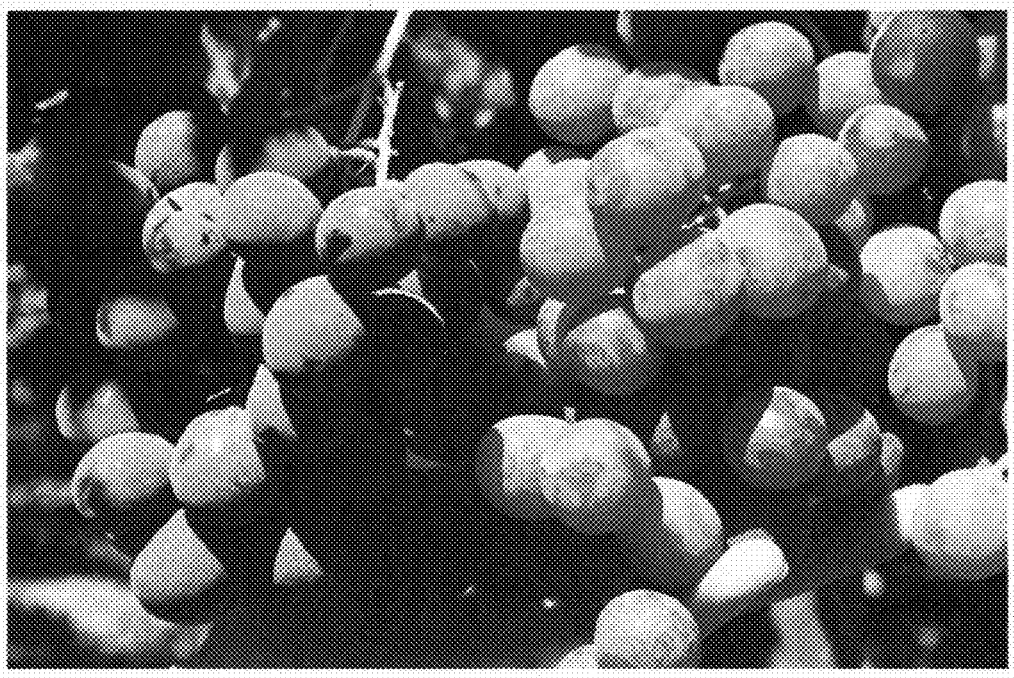
FIG. 5 shows grapes of 'Chimenti Globe' as compared to grapes of 'Red Globe' at maturity point. 'Chimenti Globe' is shown on the right, and 'Red Globe' is shown on the left.
Figure 6:
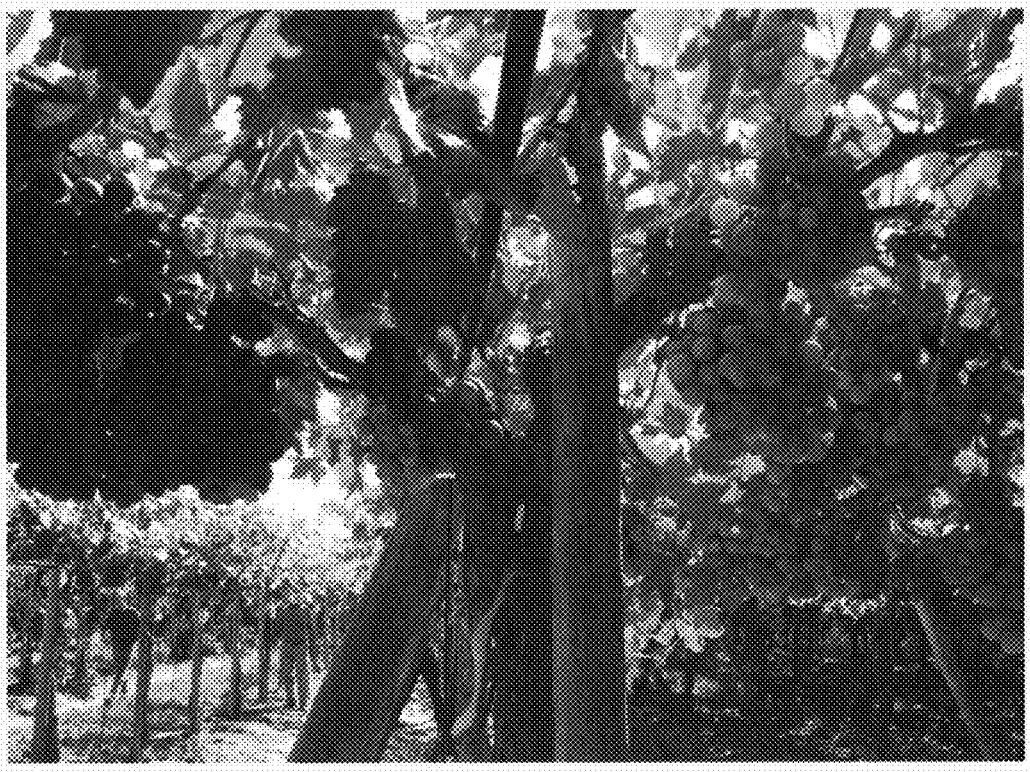
FIG. 6 shows grapes of 'Chimenti Globe' as compared to grapes of 'Red Globe' one month before harvest. 'Chimenti Globe' is shown on the right, and 'Red Globe' is shown on the left.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the 'Chimenti Globe' variety is based on the originally identified plant and asexually reproduced progeny, grown at Talagante area, Metropolitan Region of Chile.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant or any group of plants, of the new variety may vary from the stated average. Color descriptions and other terminology are used in accordance with their ordinary dictionary descriptions, unless the context clearly indicates otherwise. Color designations are made with reference to The Chilean Exporters Association (ASOEX A.G.) for 'Red Globe' grape color chart.

Throughout this specification subjective description values conform to those set forth by the International Union for the Protection of New Varieties of Plants (UPOV).

Vine:

*General.*—Size — medium grapevine size as determined on grapevines growing on a three wire vertical shoot positioned trellis with the wire (fruit zone) set at 210 cm (82.68 inches) above the ground; the vine was trained on 4 branches to produce a grapevine height of 2.10 meter (82.68 inches) and a grapevine spread of 7 $m^2$ (75.35 square feet). Vigor. — medium vigor. Vigor as measured by observation in relation to other varieties, less vigorous than Flame seedless, equivalent to 'Red Globe'. Production capacity — very good, consistent yields, up to 35 Kg. per grapevine, similar level to 'Red Globe'.

*Regularity of bearing.*—Regular. Annual spur pruning is required for reliable production, typical spur leaving two bud spurs.

*Rootstock.*—Own root.

Canes:

*Size.*—Mature canes. — Medium diameter. Medium vigor. Upright in growth habit.

*Mature canes.*—Diameter — internode base. — 14 mm (0.551 inches). Diameter — internode midpoint. — 9 mm (0.354 inches). Diameter — internode tip. — 4 mm (0.157 inches). Diameter — node base — 16 mm (0.63 inches). Diameter — node midpoint. — 12.5 mm (0.49 inches). Diameter — node tip. — 7.5 mm (0.295 inches). Internode length: Base — 5.5 cm (2.17 inches). Midpoint — 8.1 cm (3.19 inches). Tip. — 9 cm (3.54 inches). Average length of canes. — 134 cm (52.76 inches). Surface texture. — Smooth. Color of the upper surface of mature cane internode — green and red. Color of the ventral surface of mature cane internode — green and red. Color of the dorsal surface of the node — green. Color of the ventral surface of the node — green. Density of erect hair on the internodes — absent or very scarce. Length of the tendrils — medium. Dormant bud (compound bud or eye) Width. — At base of cane 7,5 mm (0.3 inches); at midpoint of cane 5 mm (0.2 inches) and at tip of cane 3,5 mm (0.14 inches). The average number of buds on a current single-season growth cane is 24. Date of bud break — September $20^{th}$. Mid season.

*Young shoots.*—Surface texture. — smooth. Diameter of young shoots in spring (measured when shoots are 70 cm (27.56 inches) — At base 9 mm (0.35 inches) at midpoint 6 mm (0.24 inches) and at tip 3 mm (0.12 inches). Young shoots: Shape — Straight to slightly curved. Shoot tip: Form. — Open. Tendrils: very thin, wiry. Shape. — Usually bifurcated and curled on distal end. Surface texture — smooth.

Leaves:

*Young leaves.*—Color of upper surface of first four distal unfolded leaves — green with anthocyanin areas. Density of prostrate hairs between veins (lower surface) — absent or very sparse. Density of prostrate hairs on veins (lower surface) — absent or very sparse.

*Mature leaf.*—Average length — about 18.1 cm (7.13 inches). Width — about 16.1 cm (6.34 inches). Mature leaf size — Large. Shape of blade — Cuneiform. Number of lobes — 5. Anthocyanic coloration of main veins on upper side of blade — absent. Mature leaf profile — Flat. Thickness. — Thin about 2 mm.

*Generally.*—Leaves simple and alternate. Lobes with ribs arched inward so three mayor lobes overlap, central lobe short, less prominent than laterals. Leaf margin — Serrated. Shape of teeth — Mixture of both sides straight sides and both sides convex. Length of teeth — Medium. Ratio length/width of teeth — medium. Depth of upper lateral sinuses — very deep. Petiole sinus. — The position of the two lobes near the petiole end is slightly open, with U shape. Density of prostrate hairs between veins on lower surface of blade — Absent. Density of erect hair between veins on lower surface of blade — Absent. Density of prostrate hairs on main veins on lower surface of blade — none or very sparse. Density of erect hairs on main veins on lower surface of blade — None or very sparse. Density of erect hairs on main veins on lower surface of blade — None or very sparse. Density of prostrate hairs on main veins on upper surface of blade — None or very sparse. Density of erect hairs on main veins on upper surface of blade — None. General shape petiole sinus — slightly open — Lobes slightly overlapping. Shape of the petiole sinus — U shaped. Anthocyanin coloration of main veins — Absent or very low red on main veins near center of leaf. Surface appearance — retains some glossiness. Blistering surface of blade — Medium. Petiole: Size. — Medium. Length — 13.0 cm (5.12 inches). Length of the petiole compared to middle vein — slightly shorter. Surface texture. — smooth.

Trunk: Slender and straight.

*Size.*—Height. — Approximately 1.95 cm (76,77 inches) above the vineyard floor. Diameter. — 6,5 cm (2,56 inches) as measured just over the grafting area at 120-130 cm (47,24-51,18 inches) above vineyard floor, on grafts 4 years old.

Flowers:

*General.*—Flower sex — Hermaphrodite. : Size — generally. — Medium Unopened — diameter. — 1.7 mm (0.066 inches). Unopened — length. — 1.8 mm (0.07 inches). Unopened — surface texture. — Smooth. Date of bloom. — First bloom November 11. Date of full bloom. — November 24 at 90%.

*Inflorescence.*—Fragrance: no fragrance. — Cluster size: At bloom. — Generally. Medium. Cluster — length. — 14.1 cm (5.55 inches). Width. — 12.7 cm (5 inches). Pollen — normal — fertile — abundant. Bearing inflorescent at second node, occasionally a small additional one at node three; inflorescence very narrow, with very slender peduncle, flower with very small pistil, stamens diverging, filaments rigid.

Fruit:

*General use.*—Fresh fruit market.

*Ripening period.*—Late season: Ripe for commercial harvesting and shipment approximately March 12 in Talagante, Chile.

*Keeping quality.*—Excellent.

*Resistance to.*—Insects: average typical of *Vitis vinifera* species; diseases: average typical of *Vitis vinifera* species.

*Shipping quality.*—Good. Refractometer test — Solid — sugar: about 20° Brix. Acidity — about 0,40%. Juice pH — About 3,6.

*Cluster* (*Bunch*).—Mature cluster Length. — About 22 cm (8.66 inches). Mature cluster Width. — About 15,5 cm (6.1 inches). Mature cluster weight — 900 grams: Shape. — Conical. Bunch Density — Slightly dense, requires thinning with gibberellic acid. Number of berries — about 85 berries per cluster (hand thinned). Length of peduncle — long, approximately 9,5 cm (3.74 inches) from attachment to first branch of main rachis. Usually straight. Lignification of peduncle — Brown about 1.5 cm (0.59 inches) at base. Clusters per vine. 30-32.

*Berry*.—Uniformity of size — uniform. Berry size — very large. Single berry weight — about 11 Grams. Single berry diameter: 26 mm-30 mm. (1.02-1.18 inches) Shape — wide ellipsoid. Berry dimensions — longitudinal axis: About 20,6 cm (8.11 inches), horizontal axis: About 24,9 cm (9.8 inches). Skin color (without bloom) — Pink (Plate RG1 ASOEX). Berry firmness — soft to slightly firm. Particular flavor — different from herbaceous — no astringent. Bloom (cuticular wax) — moderate. Berry separation from pedicel — difficult. Skin. — thickness — medium. Texture of flesh — Medium firm and meaty. Anthocyanic pigmentation of pulp — Absent or very weak, color is light cream green with small pigmentation of light red. Reticulation — Absent. Seed — contains 2-4 large seeds per berry. Seeds are 3 mm×8 mm (0.12-0.31 inches) when dried. Seed color is pale, and are soft to eat and of neutral flavor. Seed shape — triangular in cross section.

The variety has no particular disease or insect resistance and is similar in susceptibility to other commonly grown *Vitis vinifera* varieties. It therefore, requires similar protective measures as other common varieties to be grown commercially.

I claim:

1. A new and distinct variety of table grape designated 'Chimenti Globe' as shown and described herein.

* * * * *